United States Patent
Aouak et al.

(10) Patent No.: US 11,617,989 B1
(45) Date of Patent: Apr. 4, 2023

(54) EXTRACTION OF BENZENE FROM BENZENE/CYCLOHEXANE MIXTURE

(71) Applicant: KING SAUD UNIVERSITY, Riyadh (SA)

(72) Inventors: Taieb Aouak, Riyadh (SA); Mohamed Ouladsmane, Riyadh (SA); Ahmed Yacine Badjah Hadj Ahmed, Riyadh (SA); Zeid Abdullah Alothman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 17/013,509

(22) Filed: Sep. 4, 2020

(51) Int. Cl.
*B01D 71/70* (2006.01)
*C07C 7/177* (2006.01)
(Continued)

(52) U.S. Cl.
CPC ......... *B01D 61/362* (2013.01); *B01D 5/0072* (2013.01); *B01D 69/141* (2013.01);
(Continued)

(58) Field of Classification Search
None
See application file for complete search history.

(56) References Cited

U.S. PATENT DOCUMENTS 3,140,256 A * 7/1964 Martin .................... B01D 71/18
585/818
4,758,348 A * 7/1988 Matsui ................. B01D 61/362
210/500.35
(Continued)

FOREIGN PATENT DOCUMENTS

CN 1748845 A 3/2006
CN 1748846 A 3/2006
(Continued)

OTHER PUBLICATIONS

Acharya et al., "Separation of liquid benzene/cyclohexane mixtures by perstraction and pervaporation," Journal of Membrane Science, vol. 37, Issue 3, Jun. 1988, pp. 205-232. Abstract only.
(Continued)

*Primary Examiner* — Tam M Nguyen
(74) *Attorney, Agent, or Firm* — Nath, Goldberg & Meyer; Richard C. Litman

(57) ABSTRACT

The extraction of benzene from benzene/cyclohexane mixture described herein is a process that removes benzene from a benzene/cyclohexane mixture with high selectivity, resulting in an enriched cyclohexane content in the retentate. The process involves adding an aqueous solution of poloxamer 188 to the benzene/cyclohexane mixture and waiting for the mixture to partition into an organic layer above an aqueous layer. Benzene, being more polar than cyclohexane, is selectively drawn into the aqueous layer. Benzene is then removed from the aqueous layer by pervaporation through a composite PDMS (polydimethylsiloxane)/polystyrene membrane. Cyclohexane is recovered from the retentate by drawing off the organic layer of the retentate by any known method. About 97% of benzene has been removed from a 50-50 wt % mixture by pervaporation in the static mode, and about 99% by pervaporation in the continuous mode.

15 Claims, 3 Drawing Sheets

(51) Int. Cl.
*B01D 61/36* (2006.01)
*B01D 69/14* (2006.01)
*C07C 7/144* (2006.01)
*B01D 5/00* (2006.01)
*C07C 15/04* (2006.01)

(52) U.S. Cl.
CPC .............. *B01D 71/70* (2013.01); *C07C 7/144* (2013.01); *C07C 15/04* (2013.01)

(56) References Cited

U.S. PATENT DOCUMENTS

| | | | | |
|---|---|---|---|---|
| 7,357,836 | B2* | 4/2008 | Tsapatsis | B01D 67/0051 117/68 |
| 7,717,273 | B2* | 5/2010 | Kozlov | B01D 71/82 210/500.27 |
| 2008/0312485 | A1* | 12/2008 | Takai | C12P 5/026 585/640 |
| 2011/0163002 | A1* | 7/2011 | White | B01D 71/54 208/95 |
| 2012/0074043 | A1 | 3/2012 | Kalakkunnath et al. | |
| 2014/0364567 | A1* | 12/2014 | Balsara | B01D 61/027 525/106 |
| 2015/0021261 | A1* | 1/2015 | Shiotani | D06M 15/333 210/500.23 |
| 2017/0216781 | A1* | 8/2017 | Okabe | B01D 71/42 |
| 2017/0326486 | A1* | 11/2017 | Chu | D04H 1/728 |
| 2019/0241472 | A1* | 8/2019 | Kondratowicz | C04B 28/006 |
| 2020/0391162 | A1* | 12/2020 | Zhu | B01D 53/02 |

FOREIGN PATENT DOCUMENTS

| | | |
|---|---|---|
| CN | 101091877 A | 12/2007 |
| CN | 102728248 A | 10/2012 |
| CN | 105367733 A | 3/2016 |
| JP | 02139023 A | 5/1990 |
| JP | 0398632 A | 4/1991 |
| JP | 06220040 A | 8/1994 |

OTHER PUBLICATIONS

Villaluenga et al., "A review on the separation of benzene/cyclohexane mixtures by pervaporation process," Journal of Membrane Science, vol. 169, Issue 2, May 1, 2000, pp. 159-174. Abstract only.
Chen et al., "Pervaporation performance of polydimethylsiloxane membranes for separation of benzene/cyclohexane mixtures," Applied Polymer, vol. 112, Issue 4, May 15, 2009, pp. 2425-2433. Abstract only.
Wu et al. "Synthesis and properties of polystyrene/polydimethylsiloxane graft copolymers." Frontiers of Chemistry in China 1.3 (2006): 350-356.
Dong et al., "Pervaporation separation of benzene/cyclahexane through AAOM-ionic liquids/polyurethane membranes", Chemical Engineering and Processing: Process Intensification (2015), vol. 89, pp. 62-69 (Abstract only).
Rynkowska et al., "Application of polymer-based membranes containing ionic liquids in membrane separation processes: a critical review", Rev. Chem. Eng. (2018), 34(3), pp. 342-363.
Tao Xi et al., "Morphology and pervaporation performance of ionic liquid and waterborne polyurethane composite membranes", RSC Adv. (2018), vol. 8, 7792-7799.

\* cited by examiner

EXTRACTION OF BENZENE FROM BENZENE/CYCLOHEXANE MIXTURE

BACKGROUND

1. Field

The disclosure of the present patent application relates to the removal of benzene from a benzene/cyclohexane mixture to produce a high yield of cyclohexane, and particularly to the extraction of benzene from benzene/cyclohexane mixture by pervaporation technique using a biphasic membrane.

2. Description of the Related Art

Cyclohexane is an important industrial chemical which is usually obtained by catalytic hydrogenation of benzene. Removal of residual benzene from the reaction mixture is very important in this process. However, because of the close boiling points of these components and the presence of an azeotropic point in the mixture, it is very difficult to separate cyclohexane from the benzene/cyclohexane mixture by conventional methods. Different researchers have tried to solve this problem, but the results are still insufficient. Separation processes using extractive distillation are commercially employed to solve this type of separation. However, this technique suffers from process complexity, a low selectivity/flux ratio, and high energy consumption.

Recent efforts to address the problem have focused on efforts to improve the extractive distillation technique and on improved composite membranes for extraction of benzene by pervaporation technique. While some improvements have been claimed, the purity of the resulting cyclohexane yield is not optimal, and the processes require the difficult and uneconomical synthesis of intermediates and are conducted at elevated temperatures.

Thus, a procedure for the extraction of benzene from benzene/cyclohexane mixture solving the aforementioned problems is desired.

SUMMARY

The extraction of benzene from benzene/cyclohexane mixture described herein is a process that removes benzene from a benzene/cyclohexane mixture with high selectivity, resulting in an enriched cyclohexane content in the retentate. The process involves adding an aqueous solution of poloxamer 188 to the benzene/cyclohexane mixture and waiting for the mixture to partition into an organic layer above an aqueous layer. Benzene, being more polar than cyclohexane, is selectively drawn into the aqueous layer. Benzene is then removed from the aqueous layer by pervaporation through a composite PDMS (polydimethylsiloxane)/polystyrene membrane. Cyclohexane is recovered from the retentate by drawing off the organic layer of the retentate by any known method. About 97% of benzene has been removed from a 50-50 wt % mixture by pervaporation in the static mode, and about 99% by pervaporation in the continuous mode.

The inventors refer to this technique as selective extraction of benzene from benzene/cyclohexane mixture by pervaporation technique using a biphasic membrane, namely, a solid phase PDMS/polystyrene layer and a liquid phase aqueous poloxamer layer disposed above the solid layer. Alternatively, the process may be viewed as a two-stage extraction including liquid-liquid extraction to remove cyclohexane in an organic layer, followed by membrane extraction by pervaporation to remove benzene from the remaining aqueous layer.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The extraction of benzene from benzene/cyclohexane mixture involves two steps. The first one corresponds to the partition of each component between the organic phase containing the feed and the aqueous phase. The solubility of the most polar compound, which is benzene in the present application, in water will be higher compared to that of cyclohexane. Therefore, the aqueous layer will be rich in benzene. Thus, in the second step, a higher amount of benzene will diffuse through the solid membrane to the permeate. This continuous process will result in a selective extraction of benzene while the feed is enriched in cyclohexane.

Figure 1:
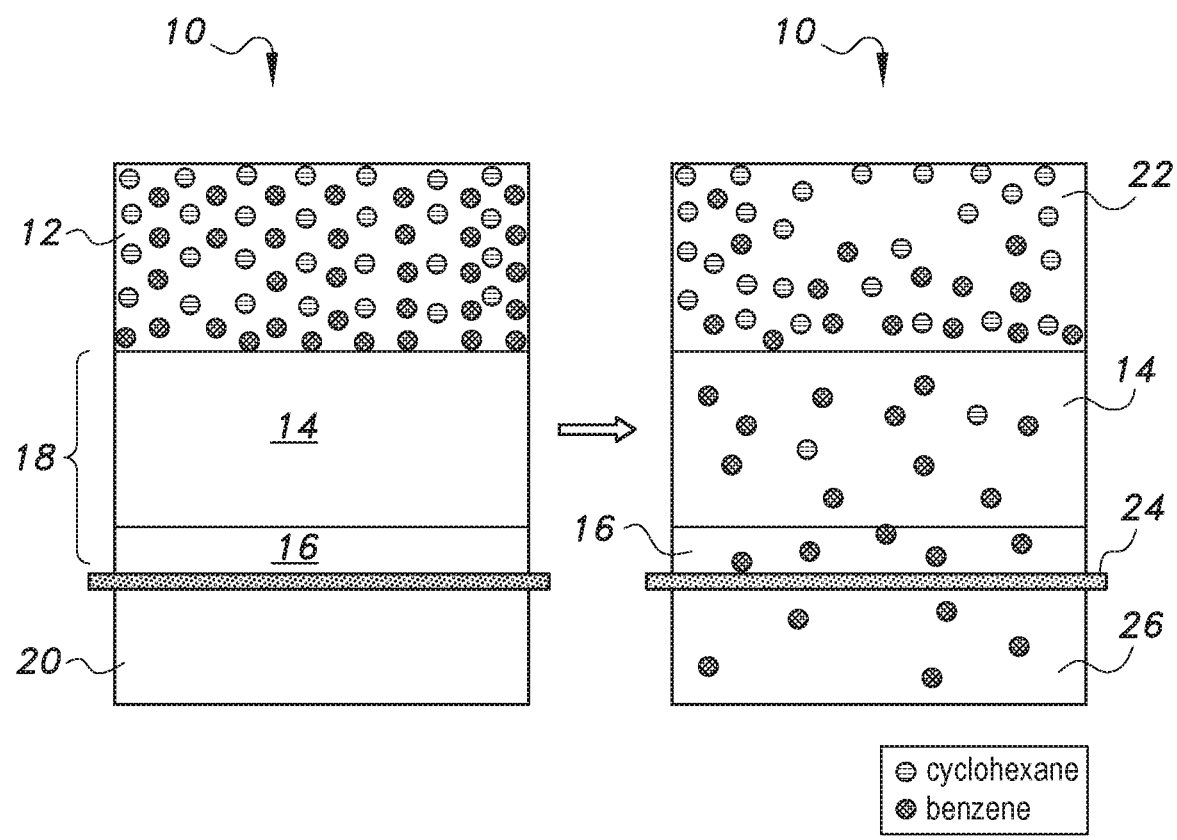
FIG. 1 is a reaction scheme for the extraction of benzene from benzene/cyclohexane mixture, shown diagrammatically.

As shown in FIG. 1, in the first step, the liquid phase 14 is an aqueous solution of between 2 wt % and 10 wt % poloxamer 188 is mixed with a feed mixture 12 of benzene/cyclohexane in the upstream compartment of a pervaporation cell 10. The benzene/cyclohexane mixture 12 partitions into an organic layer composed primarily of cyclohexane (the retentate 22, while the benzene is extracted into the aqueous poloxamer solution 14. The aqueous poloxamer layer is denser than cyclohexane so that the organic layer rises to the top of the upstream compartment, while the benzene enriched aqueous layer settles to the bottom of the upstream compartment. The bottom of the upstream compartment is formed by a solid membrane 16 made from a PDMS (polydimethylsiloxane)-polystyrene copolymer mounted on a porous support 24 above the downstream compartment 20 of the pervaporation cell 10. The aqueous poloxamer liquid phase 14 and the solid phase PDMS-polystyrene membrane, in combination, form what the inventors refer to as a bi-phasic pervaporation membrane 18. Alternatively, the extraction process may be viewed as a two-stage process, in which the first stage is the liquid-liquid extraction of benzene into the aqueous poloxamer solution 14, which serves as the extraction solvent.

In the second step, a vacuum is applied to the downstream compartment 20. The PDMS-polystyrene membrane 24 is hydrophobic, thereby resisting passage of water through the membrane 24 and selectively drawing benzene in the vapor phase (the permeate 26) into the downstream compartment 20 by pervaporation. Using this procedure, benzene was selectively extracted from a 50/50 (by volume) mixture of benzene/cyclohexane at high flux and moderate temperature (between 25-30° C.). The pervaporation parameters in terms of flux and selectivity at 25° C. varied, depending on the characteristics of the membrane used.

In the static mode, the following results were obtained: total flux: 2.22-2.85 kg·m$^{-2}$·h$^{-1}$; separation factor: 1191.34-531.3256; benzene concentration: 97.18-95.85 wt %. In the continuous mode, the results were: total flux: 2.78-3.18 kg·m$^{-2}$·h$^{-1}$; separation factor: 115.24-35.32; benzene concentration: 99.23-97.54 wt %.

The extraction of benzene from benzene/cyclohexane mixture will be better understood by reference to the following examples.

Example 1

Preparation of Aqueous Poloxamer Liquid Phase

In the experiments we performed, the poloxamer used was poloxamer-188 grade (Sigma-Aldrich) soluble in water and having average molecular weight localized between 7680 and 9510 g mol$^{-1}$ distributed in form of block on the molecular chains as 75-85 units of ethylene oxide and 25-40 propylene oxide units. Poloxamers are triblock polymers having a central block of hydrophobic polyoxypropylene and blocks of hydrophilic polyoxyethylene on opposite ends of the polyoxypropylene block. The first two digits multiplied by 100 give the approximate molecular weight of the polyoxypropylene and the last digit multiplied by 10 gives the percentage polyoxyethylene content.

Poloxamer-188 grade (Sigma-Aldrich), soluble in water and having average molecular weight of 8,000 g/mol distributed in form of block on the molecular chains as 75-85 units of ethylene oxide and 25-40 propylene oxide units was used. Liquid phase was prepared by dissolution with stirring of a known amount of poloxamer-188 in distilled water at temperature of 50° C. Three liquid phases containing different concentrations (2, 5 and 10 wt %) were prepared by this same route, as follows: POLAQ-1: 2 wt % of poloxamer-188 dissolved in water; POLAQ-2: 5 wt % of poloxamer-188 dissolved in water; POLAQ-3: 10 wt % of poloxamer-188 dissolved in water.

Example 2

Preparation of PDMS-Polystyrene Membranes

The solid phase PDMS-polystyrene membranes were prepared as follows. Cyclohexane and tetrahydrofuran were distilled with sodium under gas nitrogen. Vinyldimethylchlorosilane was distilled with calcium hydride and dried in molecular sieves. n-Butyllithium 2.5 M in hexanes was used as purchased. Styrene and divinyl benzene purchased from Sigma-Aldrich company were purified from hydroquinone (inhibitor) by distillation under reduced pressure and stored in nitrogen gas atmosphere before use.

PDMS (polydimethylsiloxane) macromonomer was prepared from its homolog cyclic trimer (D3) and vinyldimethylchlorosilane in presence of n-Butyllithium according to the procedure described in Ningjing et al., "Synthesis and properties of polystyrene/polydimethylsiloxane graft copolymers", Frontiers of Chemistry in China (2006), 1(3), 350-356. Briefly, hexamethylcyclotrisiloxane (D3) in cyclohexane was introduced to a reaction flask, and the n-butyllithium was introduced to initiate polymerization. After about 0.5 hours, 20% (by volume) N,N-dimethylformamide was added to promote propagation. Polymerization was terminated with vinylchlorosiloxane. The product was precipitated in methanol and dried under reduced pressure at 60° C. This chemical was used without further purification.

The copolymerization of PDMS macromonomer with styrene was carried out by free radical route in presence of 0.1 wt % of azobisisobutyronitrile under UV radiation (300 nm, 1000 w) during 5 h in nitrogen gas atmosphere. The reaction mixture was then poured over a Teflon Petri dish then placed in the UV reactor.

The film membrane obtained were washed with hexane and dried in air during 48 h, then in a vacuum oven for 24 h to remove all traces of residual monomers. The PDMS content in the copolymer varied between 5 and 25 wt % depending on the initial composition PDMS/Polystyrene. The yield of the copolymer obtained varied between 62 and 82 wt %.

Using this method, three membranes containing different compositions (PDMS-PS1, PDMS-PS2 and PDMS-3) were prepared and characterized by FTIR, solid NMR and DSC methods, including the following: PDMS-PS1: 94.5 wt % PDMS graft with 5.5 wt % PS; PDMS-PS2: 92.4 wt % PDMS graft with 7.5 wt % PS; and PDMS-PS3: 90.2 wt % PDMS graft with 9.8 wt % PS.

Example 3

Extraction by Pervaporation in Static Mode

The separation of benzene/cyclohexane mixture was carried out by pervaporation technique using a solid-liquid biphasic membrane 18 [PDMS-PS/poloxamer aqueous solution] at 30° C. using both the static and the dynamic modes. The thickness of the solid phase membranes varied between 250 and 325 μm and that of the liquid phase varied between 1.0 and 2.0 cm.

In this process, a determined amount of the benzene/cyclohexane mixture is placed in the upstream compartment of the membrane. The selective extraction of the solute through the pervaporation membrane leads to a gradual decrease in its concentration in the feed until its exhaustion. The pervaporation apparatus for the static mode is shown in FIG. 2.

Figure 2:
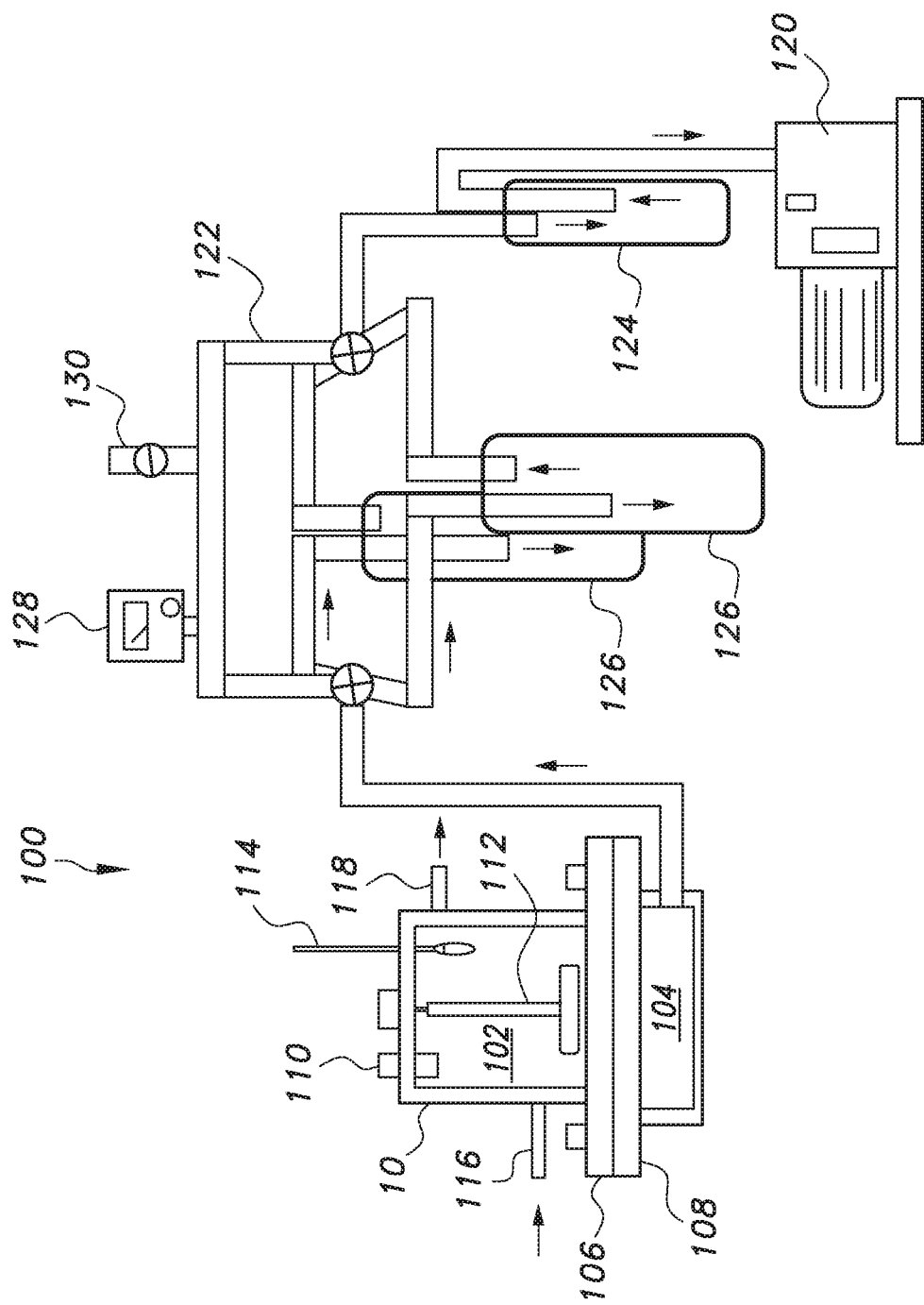
FIG. 2 is a schematic diagram of a pervaporation apparatus for the extraction of benzene from benzene/cyclohexane mixture, shown configured for operation in the static mode.

As shown in FIG. 2, the pervaporation apparatus 100 for operation in the static mode includes a double-walled pervaporation cell 10. The pervaporation cell 10 includes an upstream compartment 102 separated from a downstream compartment 104 by a solid phase PDMS-polystyrene membrane 106 mounted on a porous support 108. The benzene/cyclohexane feed and the aqueous poloxamer solution are introduced into the upstream compartment 102 though an inlet port 110 in the top wall of the cell 10 at the beginning of the extraction process. A mechanical stirrer 112 is provided for stirring the extraction mixture, and a thermometer 114 is provided for monitoring the temperature of the extraction mixture. The extraction mixture is maintained at a constant temperature by a stream of water entering through a water inlet 116, flowing through the double walls of the cell 10, and exiting through a water outlet 118.

After partitioning of the benzene into the aqueous poloxamer solvent, a vacuum is applied to the downstream compartment 104 by a vacuum pump 120 through a conduit system 122. A trap 124 protects the vacuum pump 124 from any residual benzene vapor. The conduit system 122 includes a series of cold traps 126 where benzene vapor drawn through the hydrophobic PDMS-PS membrane is condensed to liquid vapor, and may be removed from the apparatus 100. Pressure in the conduit system 122 is monitored by a Pirani gauge 128, and excessive pressure may be relieved through a Rotaflot safety valve 130.

The PDMS-PS membrane 106 (solid phase) is placed and fixed on stainless porous support 108 at the place indicated in FIG. 2. Equal volumes of benzene and cyclohexane were mixed together and introduced into the upstream part of the cell. After this, a volume of a poloxamer-188 aqueous solution (liquid phase) equal to the sum of the two organic compounds is than added under continuous stirring. After about 10 min of waiting, the separation process started. At intervals, the permeate and small amounts of retentate are taken, weighed (permeate) and analyzed by gas chromatography in which the flux and selectivity are recorded.

The performance of the membrane system was obtained with PDMS-PS1 during 4 h of the pervaporation process and at 30° C. The starting composition of the benzene/cyclohexane mixture was 50:50 wt % in the feed and some results obtained are showed in Table 1.

The total flux J and the separation factor $\alpha_{1,2}$ were evaluated from Eq. (1) and Eq. (2), respectively, and some results obtained are shown in Table 1. The equations include:

$$J = \frac{m}{s \cdot t}, \quad (1)$$

where m, s and t are the mass of permeate in kilograms, the surface area of the membrane in square meters and the time of the pervaporation process in hours, respectively; and $$\alpha_{1,2} = \frac{Y_1/Y_2}{X_1/X_2}, \quad (2)$$

where $Y_1$ and $Y_2$ are the mole fractions of the components 1 and 2 in the permeate 26, and $X_1$ and $X_2$ are the mole fractions of the components 1 and 2 in the retentate 22.

TABLE 1

Extraction of benzene from benzene/cyclohexane: Static mode

| Membrane | Flux (kg m$^{-2}$ h$^{-1}$) | Benzene (wt %) | Cyclohexane (wt %) | Separation factor, $\alpha_{1,2}$ |
|---|---|---|---|---|
| PLOLAQ-1/ PDMS-PS1 | 2.22 | 97.18 | 2.82 | 1191.34 |
| PDMS-PS3/ PDMS-PS3 | 2.85 | 95.87 | 4.13 | 531.56 |

Component 1: benzene; Component 2: cyclohexane

Example 4

Extraction by Pervaporation in Static Mode

In this process, the upstream part of the membrane is directly connected to a reservoir containing a large quantity of the organic mixture in which the mixture in this compartment is continually renewed by circulation provided by a peristaltic pump. In this situation, the concentration of the charge is maintained practically constant during the pervaporation process. A pervaporation apparatus for operation in the dynamic mode is shown in FIG. 3.

Figure 3:
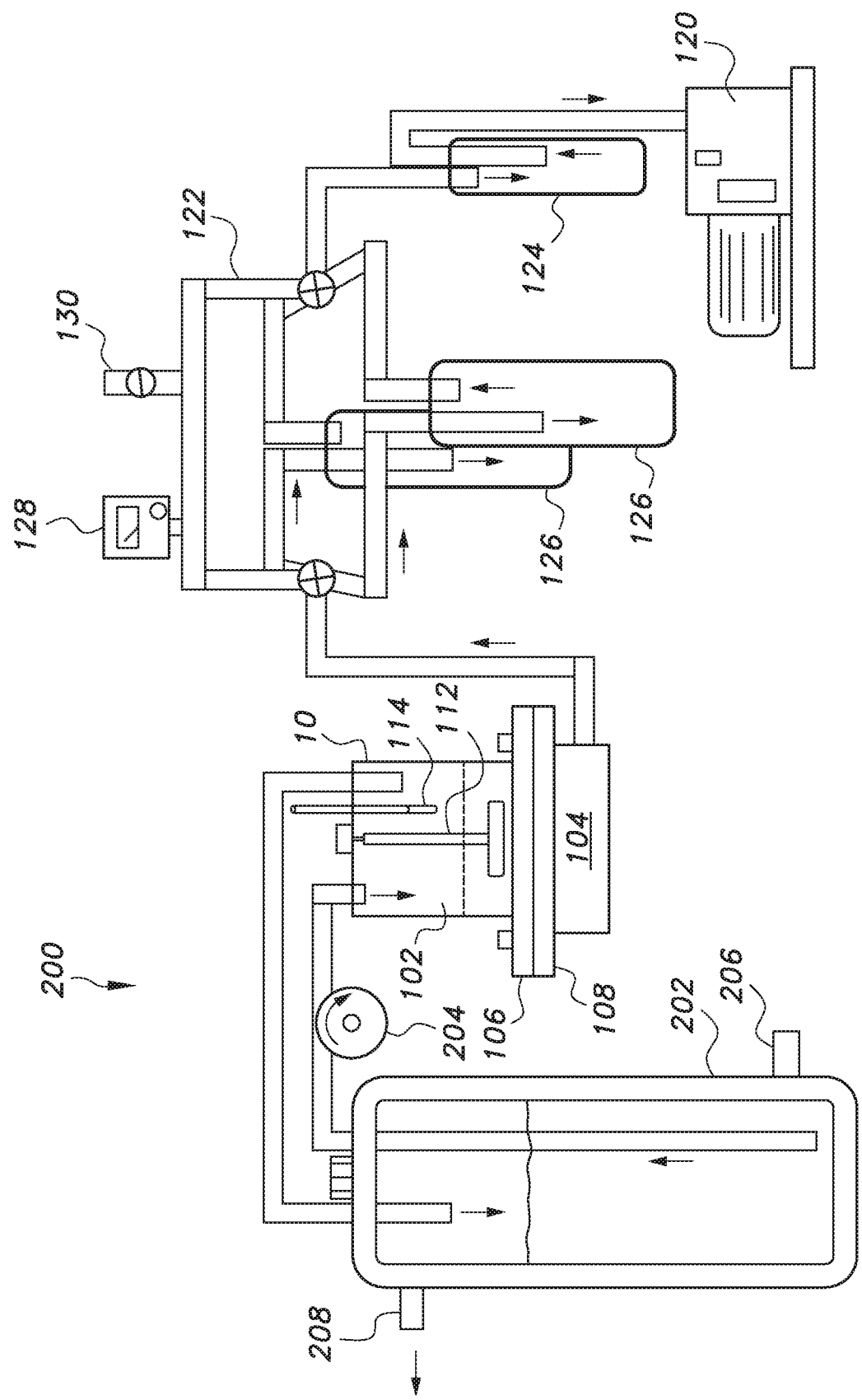
FIG. 3 is a schematic diagram of a pervaporation apparatus for the extraction of benzene from benzene/cyclohexane mixture, shown configured for operation in the dynamic mode.

As shown in FIG. 3, the pervaporation apparatus 200 for operation in the dynamic mode is very similar to the pervaporation apparatus of FIG. 2. However, the apparatus 200 in FIG. 3 also includes a reservoir 202 connected to the pervaporation cell 10 by conduit including a peristaltic pump 204 that maintains the feed of benzene/cyclohexane at a constant vol/vol ratio of 50/50. The reservoir 202 is a double-walled vessel with a water inlet 206 and a water outlet 208 to maintain a constant flow of water between the inner and outer walls to maintain the reserve of feed at the desired extraction temperature. Otherwise, the structure and operation of the pervaporation apparatus 200 of FIG. 3 are similar to the pervaporation apparatus 100 of FIG. 2.

The PDMS-PS membrane 106 (solid phase) is placed and fixed on stainless porous support 108 at the place indicated in the drawing. Equal volumes of benzene and cyclohexane were mixed together and introduced into the reservoir 202 (tank) (10 liters). The feed is then transferred in the upstream part 102 of the cell 10, then continually renewed using the peristaltic pump 204 placed on the supply tube, as indicated in FIG. 3. After this, a volume of a poloxamer-188 aqueous solution (liquid phase) equal to the sum of the two organic compounds is than added under continuous stirring. After about 10 min of waiting, the separation process started. At interval times, the permeate and small amounts of retentate are taken, weighed (permeate), and then analyzed by gas chromatography, in which the flux and selectivity are recorded.

The performance of the membrane system was obtained with PDMS-PS1 during 4 h of the pervaporation process and at 25° C. The starting composition of the benzene/cyclohexane mixture was 50:50 wt %, which is close to the azeotropic composition, in the feed and practically maintained constant during this period. Exemplary results are show in Table 2.

TABLE 2

Extraction of benzene from benzene/cyclohexane: Static mode

| Membrane | Flux (kg m$^{-2}$ h$^{-1}$) | Benzene (wt %) | Cyclohexane (wt %) | Separation factor, $\alpha_{1,2}$ |
|---|---|---|---|---|
| PLOLAQ-1/ PDMS-PS1 | 2.78 | 99.23 | 0.77 | 115.24 |
| PDMS-PS3/ PDMS-PS3 | 3.18 | 97.54 | 2.46 | 35.32 |

Component 1: benzene; Component 2: cyclohexane

The experiments in Examples 3 and 4 were repeated three times in the same conditions, and the values of fluxes and selectivity were taken from the average of the results obtained.

It is to be understood that the extraction of benzene from benzene/cyclohexane mixture is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for extraction of benzene from a benzene/cyclohexane mixture, comprising the steps of:
   feeding a benzene/cyclohexane mixture into an upstream compartment of a pervaporation cell, the pervaporation cell having a solid phase hydrophobic membrane supported on a porous support below the upstream compartment and a downstream compartment below the hydrophobic membrane;

adding an aqueous solution of a poloxamer to the upstream compartment with continuous stirring to form an extraction mixture;

allowing the extraction mixture to partition into an upper organic phase and a lower aqueous phase, the benzene in the benzene/cyclohexane mixture being drawn into the aqueous phase, the aqueous poloxamer phase and the solid phase hydrophobic membrane forming a biphasic pervaporation membrane having a liquid phase on top of a solid phase; and applying vacuum to the downstream compartment of the pervaporation cell, whereby benzene is selectively extracted as a vapor permeate through the biphasic pervaporation membrane into the downstream compartment, cyclohexane being retained as retentate in the upper organic layer.

2. The method for extraction of benzene according to claim 1, wherein the benzene/cyclohexane mixture fed into the upstream compartment is a 50:50 vol/vol mixture of cyclohexane and benzene.

3. The method for extraction of benzene according to claim 1, wherein the benzene/cyclohexane mixture fed into the upstream compartment is a 50:50 wt/wt mixture of cyclohexane and benzene.

4. The method for extraction of benzene according to claim 1, wherein the poloxamer comprises poloxamer 188.

5. The method for extraction of benzene according to claim 1, wherein said solid phase hydrophobic membrane comprises a polydimethylsiloxane-polystyrene (PDMS-PS) copolymer.

6. The method for extraction of benzene according to claim 1, wherein the extraction is carried out in static mode, no additional benzene/cyclohexane mixture being added after the initial feeding step.

7. The method for extraction of benzene according to claim 1, wherein the extraction is carried out in dynamic mode, additional feed of the benzene/cyclohexane mixture being added during the extraction to maintain benzene and cyclohexane in constant ratio in the upstream compartment.

8. The method for extraction of benzene according to claim 1, further comprising the steps of:
removing the benzene in vapor phase from the downstream compartment; and
condensing the benzene to liquid phase.

9. The method for extraction of benzene according to claim 1, further comprising the step of maintaining the extraction mixture at a temperature between 25° C. and 30° C. during the extraction.

10. The method for extraction of benzene according to claim 1, wherein the solid phase of the biphasic membrane has a thickness between 250 and 325 m and the liquid phase of the biphasic membrane has a thickness between 1.0 and 2.0 cm.

11. A method for extraction of benzene from a benzene/cyclohexane mixture, comprising the steps of:
selectively extracting benzene from the benzene/cyclohexane mixture by liquid-liquid extraction into an aqueous solution of poloxamer as extraction solvent; and
selectively extracting the extracted benzene from the aqueous solution of poloxamer by pervaporation through a polydimethylsiloxane-polystyrene membrane by pervaporation to complete separation of benzene from the benzene cyclohexane mixture.

12. The method for extraction of benzene according to claim 11, wherein the poloxamer comprises poloxamer 188.

13. The method for extraction of benzene according to claim 11, further comprising the step of maintaining the extraction at a temperature between 25° C. and 30° C. during the extraction.

14. The method for extraction of benzene according to claim 11, further comprising the step of condensing the pervaporated benzene from the vapor phase to liquid phase.

15. The method for extraction of benzene according to claim 11, further comprising the step of separating cyclohexane from the extraction solvent to recover substantially benzene-free cyclohexane from the mixture.

* * * * *